United States Patent
Harmer et al.

(10) Patent No.: US 6,534,690 B2
(45) Date of Patent: *Mar. 18, 2003

(54) PROCESS FOR THE PREPARATION OF SPHERICALLY SHAPED MICROCOMPOSITES

(75) Inventors: Mark Andrew Harmer, Kennett Square, PA (US); Qun Sun, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/844,236

(22) Filed: Apr. 26, 2001

(65) Prior Publication Data

US 2001/0037045 A1 Nov. 1, 2001

Related U.S. Application Data

(62) Division of application No. 09/588,528, filed on Jun. 6, 2000, now Pat. No. 6,262,326, which is a division of application No. 09/155,261, filed as application No. PCT/US97/04704 on Mar. 24, 1997, now Pat. No. 6,107,233, which is a continuation of application No. 08/623,272, filed on Mar. 28, 1996, now abandoned.

(51) Int. Cl.⁷ .............................. C07C 2/64; C07C 2/66; C07C 2/68; C07C 1/20
(52) U.S. Cl. .................. 585/446; 585/422; 585/456; 585/462; 585/469; 585/470; 585/471
(58) Field of Search ................................. 585/422, 446, 585/456, 462, 469, 470, 471

(56) References Cited

U.S. PATENT DOCUMENTS

| | | | |
|---|---|---|---|
| 2,757,073 A | 7/1956 | Drexel ........................ 23/182 |
| 3,607,777 A | 9/1971 | Winyall et al. | |
| 3,855,172 A | 12/1974 | Iler et al. | |
| 4,038,213 A | 7/1977 | McClure et al. ............. 252/430 |
| 4,433,082 A | 2/1984 | Grot ............................ 524/755 |
| 5,093,451 A | 3/1992 | Panster et al. .................. 528/9 |
| 5,094,995 A | 3/1992 | Butt et al. ................... 502/402 |
| 5,105,043 A | 4/1992 | Young ......................... 585/477 |
| 5,130,396 A | 7/1992 | Panster et al. .................. 528/9 |
| 5,472,926 A | 12/1995 | Gubitosa et al. ............ 502/337 |
| 5,824,622 A | 10/1998 | Harmer et al. ............... 502/407 |
| 5,849,974 A | 12/1998 | Clarembeau et al. ........ 585/668 |
| 5,916,837 A | 6/1999 | Harmer et al. ............... 502/170 |
| 5,932,511 A | 8/1999 | Harmer et al. ............... 502/159 |
| 5,948,946 A | 9/1999 | Harmer et al. ............... 585/669 |
| 6,034,290 A | 3/2000 | Harmer et al. ............... 570/236 |
| 6,133,493 A | * 10/2000 | Harmer et al. ............... 585/457 |
| 6,160,190 A | * 12/2000 | Harmer et al. ............... 585/458 |

FOREIGN PATENT DOCUMENTS

| | | | |
|---|---|---|---|
| CA | 2084967 | 6/1993 | ............. C07F/7/08 |
| CA | 2103653 | 2/1994 | ........... C08G/77/27 |
| EP | 0 503 688 | 9/1992 | ............ B01J/31/10 |
| GB | 1094798 | 12/1967 | |
| WO | WO95/19222 | 7/1995 | ............ B01J/31/10 |
| WO | WO96/19288 | 6/1996 | ............ B01J/31/10 |

OTHER PUBLICATIONS

J.J. Kirkland, *Chromatographic Science*, 10, 593–599, 1972, No month.

The "DEXOLAN®" Product Family, *Degussa Product Literature*, No date.

* cited by examiner

*Primary Examiner*—Elizabeth D. Wood

(57) ABSTRACT

A process for the preparation of at least one spherically shaped porous microcomposite is provided which microcomposite comprises a perfluorinated ion-exchange polymer containing pendant sulfonic and/or carboxylic acid groups entrapped within and highly dispersed throughout a network of inorganic oxide, wherein the weight percentage of the perfluorinated ion-exchange polymer in the microcomposite is from about 0.1 to about 90 percent, and wherein the size of the pores in the microcomposite is about 0.5 nm to about 75 nm; said process comprising the steps of: (a) combining a water-miscible inorganic oxide network precursor system, a water-miscible liquid composition comprising a perfluorinated ion-exchange polymer containing pendant sulfonic and/or carboxylic acid groups, and an organic liquid to form a two phase liquid system; (b) agitating the two phase liquid system sufficiently to sustain a dispersion of the water-miscible phase in the shape of spheres in the organic phase; (c) allowing the inorganic oxide network precursor system to form a network of inorganic oxide to yield at least one spherically shaped porous microcomposite having the above-described properties; and (d) recovering the at least one spherically shaped porous microcomposite.

2 Claims, No Drawings

PROCESS FOR THE PREPARATION OF SPHERICALLY SHAPED MICROCOMPOSITES

CROSS REFERENCE TO RELATED APPLICATIONS

This application is a divisional of application Ser. No. 09/588,528, filed Jun. 6, 2000, now U.S. Pat. No. 6,262,326, which is a divisional of application Ser. No. 09/155,261, filed Sep. 24, 1998, now U.S. Pat. No. 6,107,233, which was filed under 35 U.S.C. 371 from International Application No. PCT/US97/04704, filed Mar. 24, 1997, which is a continuation from U.S. application Ser. No. 08/623,272, filed on Mar. 28, 1996, now abandoned.

BACKGROUND OF THE INVENTION

The present invention relates to a process for preparing a spherically shaped microcomposite comprising a perfluorinated ion-exchange polymer containing pendant sulfonic acid groups and/or pendant carboxylic acid groups entrapped within and highly dispersed throughout an inorganic oxide network. Due to their high surface area and acid functionality, these spherically shaped microcomposites possess wide utility as improved solid acid catalysts.

A microcomposite comprising perfluorinated ion-exchange polymers containing pendant sulfonic acid groups and/or pendant carboxylic acid groups entrapped within and highly dispersed throughout a metal oxide network and its preparation are disclosed in WO95/19222. The microcomposites described therein are irregular shaped particles which can be subject to attrition. Attrition can lead to fines which can cause problems in certain filtering processes and columns, such as clogging, pressure build up and the generation of friction. Fines can also find their way into a final product in certain applications which is undesirable.

Canadian Patent Application No. 2,103,653 describes shaped organosiloxane polycondensates in the form of macroscopic spherical particles. The polycondensates described contain no perfluorinated ion exchange polymer.

It is an object of the present invention to provide a shaped microcomposite that possesses high catalytic activity, high attrition resistance, and better handling characteristics.

SUMMARY OF THE INVENTION

The present invention provides a process for the preparation of at least one spherically shaped porous microcomposite which comprises a perfluorinated ion-exchange polymer containing pendant sulfonic and/or carboxylic acid groups entrapped within and highly dispersed throughout a network of inorganic oxide, wherein the weight percentage of the perfluorinated ion-exchange polymer in the microcomposite is from about 0.1 to about 90 percent, and wherein the size of the pores in the microcomposite is about 0.5 nm to about 75 nm; said process comprising the steps of:

(a) combining a water-miscible inorganic oxide network precursor system, a water-miscible liquid composition comprising a perfluorinated ion-exchange polymer containing pendant sulfonic and/or carboxylic acid groups, and an organic liquid to form a two phase liquid system;

(b) agitating the two phase liquid system sufficiently to sustain a dispersion of the water-miscible phase in the shape of spheres in the organic phase;

(c) allowing the inorganic oxide network precursor system to form a network of inorganic oxide to yield at least one spherically shaped porous microcomposite having the above-described properties; and (d) recovering the at least one spherically shaped porous microcomposite.

DETAILED DESCRIPTION

This invention is directed to a process for preparing at least one spherically shaped porous microcomposite having a diameter of about 0.1 to about 1.0 mm, a specific surface area of about 10 to about 800 $m^2/g$, and a specific pore volume of about 0.2 to about 3.0 cc/g. The at least one spherically shaped microcomposite comprises a perfluorinated ion-exchange polymer containing pendant sulfonic and/or carboxylic acid groups entrapped within and highly dispersed throughout a network of inorganic oxide, wherein the weight percentage of the perfluorinated ion-exchange polymer in the microcomposite is from about 0.1 to about 90 percent. The size of the pores in the microcomposite is about 0.5 nm to about 75 nm. Preferably, the pore size is about 0.5 to about 50 nm, most preferably about 0.5 to about 30 nm.

In step (a) of the process of the present invention, a water-miscible inorganic oxide network precursor system is combined with a water-miscible liquid composition comprising a perfluorinated ion-exchange polymer containing pendant sulfonic and/or carboxylic acid groups, and an organic liquid to form a two phase liquid system. Although the sequence of combining the components of the two phase liquid system is not critical, preferably the water-miscible components are contacted with each other first followed by contact with the organic liquid.

The water-miscible inorganic oxide network precursor system comprises an inorganic oxide network precursor, water and optionally a catalyst.

The "inorganic oxide" signifies metallic, semimetallic or other inorganic oxide compounds, including, for example, alumina, silica, titania, germania, zirconia, aluminosilicates, zirconyl-silicates, chromic oxides, germanium oxides, copper oxides, molybdenum oxides, tantalum oxides, zinc oxides, yttrium oxides, vanadium oxides, and iron oxides. Alumina, silica, titania and zirconia are preferred, and silica is most preferred. The term "inorganic oxide network precursor" refers to an inorganic oxide precursor or an inorganic oxide initially used in the present process to yield a network of inorganic oxide in the resultant at least one spherically shaped microcomposite. Most inorganic oxide network precursors will hydrolyze and condense into the network of inorganic oxide during the course of the present process. Other inorganic oxide network precursors exist initially as an inorganic oxide, such as colloidal silica.

In the case of silica, for example, a range of silicon alkoxides can be hydrolyzed and condensed to form the network of inorganic oxide. Such inorganic oxide network precursors as tetramethoxysilane, tetraethoxysilane, tetrapropoxysilane, tetrabutoxysilane, and any compounds under the class of organic alkoxides which in the case of silicon is represented by $Si(OR)_4$, where R, which can be the same or different, includes methyl, ethyl, n-propyl, iso-propyl, n-butyl, sec-butyl, iso-butyl, tert-butyl can be used. Also included as an inorganic network precursor is silicon tetrachloride. Further inorganic oxide network precursors comprise organically modified silica, for example, $CH_3Si(OCH_3)_3$, $PhSi(OCH_3)_3$, where Ph is phenyl, and $(CH_3)_2Si(OCH_3)_2$. Other inorganic oxide network precursors include metal silicates, for example, potassium silicate, sodium silicate and lithium silicate. As an alternative to using as is, the potassium, sodium or lithium ions of these metal silicates can be removed using a DOWEX® cation exchange resin (sold by Dow Chemical, Midland, Mich.), which generates polysilicic acid which gels at slightly acid to basic pH. The use of LUDOX® colloidal silica (E. I. du Pont de Nemours and Company, Wilmington, Del.) and fumed silica (CAB-O-SIL® sold by Cabot Corporation of Boston, Mass.) which can be gelled by altering pH and adjusting the concentration of the silicon species in solution will also yield a network of inorganic oxide in the spherically shaped microcomposite of the present invention. Preferred inorganic oxide network precursors for silica are tetramethoxysilane, tetraethoxysilane and sodium silicate; and a preferred inorganic oxide network precursor for alumina is aluminum tri-secbutoxide $Al(OC_4H_9)_3$.

The amount of water used in the inorganic oxide network precursor system of the present process is at least sufficient for the complete hydrolysis and condensation of those inorganic oxide network precursors that are not already hydrolyzed and/or condensed. Preferably, an excess amount of water is used as compared with the stoichiometrically required amount. The amount of water required for hydrolysis depends on the rate of hydrolysis of each inorganic oxide network precursor used. Generally, hydrolysis takes place more rapidly with increasing amounts of water. Hydrolysis can begin upon contact of the inorganic oxide network precursor with the water.

The amount of water needed in the inorganic oxide network precursor system when inorganic oxides, such as colloidal silica, are used as the inorganic oxide network precursor is that which is sufficient to provide a water-miscible system upon its contact with the inorganic oxide network precursor.

Optionally, the water-miscible inorganic oxide precursor system may further comprise a catalyst. Representative examples of suitable catalysts are HCl, $H_3PO_4$, $CH_3COOH$, $NH_3$, $NH_4OH$, NaOH, KOH and $NR^1_3$, wherein $R^1$ represents an alkyl group which contains 1 to 6 carbon atoms. The catalyst can be added with stirring.

The temperature during formation of the water-miscible inorganic oxide network precursor system can range from about 0° C. to about 100° C. Atmospheric pressure can be used.

Agitation, such as by stirring or ultrasonication, should be used, if necessary, to effect good contact of the inorganic oxide network precursor with the water and with the optional catalyst. Agitation may not be required for the formation of every inorganic oxide network precursor system.

The water-miscible liquid composition comprising a perfluorinated ion exchange polymer (PFIEP) containing pendant sulfonic acid, carboxylic acid, or sulfonic acid and carboxylic acid groups used in the present invention are well known compounds. See, for example, Waller et al., Chemtech, July 1987, pp. 438–441, and references therein, and U.S. Pat. No. 5,094,995, incorporated herein by reference. PFIEP containing pendant carboxylic groups have been described in U.S. Pat. No. 3,506,635, which is also incorporated by reference herein. Polymers discussed by J. D. Weaver et al., in Catalysis Today, 14 (1992) 195–210, are also useful in the present invention. Polymers that are suitable for use in the present invention have structures that include a substantially fluorinated carbon chain that may have attached to it side chains that are substantially fluorinated. In addition, these polymers contain sulfonic acid groups or derivatives of sulfonic acid groups, carboxylic acid groups or derivatives of carboxylic acid groups and/or mixtures of these groups. For example, copolymers of a first fluorinated vinyl monomer and a second fluorinated vinyl monomer having a pendant cation exchange group or a pendant cation exchange group precursor can be used, e.g. sulfonyl fluoride groups ($SO_2F$) which can be subsequently hydrolyzed to sulfonic acid groups. Possible first monomers include tetrafluoroethylene (TFE), hexafluoropropylene, vinyl fluoride, vinylidine fluoride, trifluoroethylene, chlorotrifluoroethylene, perfluoro (alkyl vinyl ether), and mixtures thereof. Possible second monomers include a variety of fluorinated vinyl ethers with pendant cation exchange groups or precursor groups. Preferably, the polymer contains a sufficient number of acid groups to give an equivalent weight of from about 500 to 20,000, and most preferably from 800 to 2000. Representative of the perfluorinated polymers, for example, are those used in membranes, such as NAFION®, commercially available from E. I. du Pont de Nemours and Company), and polymers, or derivatives of polymers, disclosed in U.S. Pat. Nos. 3,282,875; 4,329,435; 4,330,654; 4,358,545; 4,417,969; 4,610,762; 4,433,082; and 5,094,995. More preferably the polymer comprises a perfluorocarbon backbone and a pendant group represented by the formula $-OCF_2CF(CF_3)OCF_2CF_2SO_3X$, wherein X is H, an alkali metal or $NH_4$. Polymers of this type are disclosed in U.S. Pat. No. 3,282,875.

Typically, suitable perfluorinated polymers are derived from sulfonyl group-containing polymers having a fluorinated hydrocarbon backbone chain to which are attached the functional groups or pendant side chains which in turn carry the functional groups. Fluorocarbosulfonic acid catalysts polymers useful in preparing the spherically shaped microcomposites of the present invention have been made by Dow Chemical and are described in Catalysis Today, 14 (1992) 195–210. Other perfluorinated polymer sulfonic acid catalysts are described in Synthesis, G. I. Olah, P. S. Iyer, G. K. Surya Prakash, 513–531 (1986).

There are also several additional classes of polymer catalysts associated with metal cation ion-exchange polymers and useful in preparing the at least one spherically shaped microcomposite of the present invention. These comprise 1) a partially cation-exchanged polymer, 2) a completely cation-exchanged polymer, and 3) a cation-exchanged polymer where the metal cation is coordinated to another ligand (see U.S. Pat. No. 4,414,409, and Waller, F. J. in Polymeric Reagents and Catalysts; Ford, W. T., Ed.; ACS Symposium Series 308; American Chemical Society; Washington, D.C., 1986, Chapter 3).

Preferred PFIEP suitable for use in the present invention comprise those containing sulfonic acid groups, such as a sulfonated PFIEP prepared from a NAFION® solution. More preferred is a PFIEP prepared from resins having an equivalent weight of about 800 to 2000 comprising tetrafluoroethylene and perfluoro(3,6-dioxa-4-methyl-7-octenesulfonyl fluoride).

PFIEP are used within the context of the present invention in a liquid composition form (also commonly called solutions) which can be prepared using the process in U.S. Pat. No. 4,433,082 or Martin et al., Anal. Chem., Vol. 54, pp 1639–141(1982) incorporated by reference herein. Solvents and mixtures other than those in U.S. Pat. No. 4,433,082 and Martin et al. may also be effective in preparing the liquid composition of PFIEP. The liquid composition of PFIEP can be used directly and may be filtered through fine filters (e.g., 4–5.5 micrometers) to obtain clear, though perhaps slightly colored, solutions. The liquid compositions of PFIEP obtained by these processes can be further modified by removing a portion of the water, alcohols and any volatile organic by-products by distillation, e.g. to give a liquid composition containing water only.

Commercially available liquid compositions of perfluorinated ion-exchange polymer can also be used in the preparation of the at least one spherically shaped microcomposite of the present invention (e.g., a 5 wt % solution of a perfluorinated ion-exchange powder in a mixture of lower aliphatic alcohols and water, Cat. No. 27,470-4, Aldrich Chemical Company, Inc., 940 West Saint Paul Avenue, Milwaukee, Wis. 53233).

Optionally, the liquid composition comprising PFIEP may further comprise an acid or base catalyst. The catalyst acts to allow network formation of the water-miscible inorganic oxide network precursor system via gelation to occur, and/or it increases the rate of gelation once in the presence of the water-miscible inorganic oxide network precursor system.

Formation of the liquid composition comprising PFIEP can be made at a temperature ranging from about 0° C. to about 100° C. Atmospheric pressure can be used. Some agitation may be required to obtain good contact between the liquid composition of PFIEP and the catalyst that can optionally be added.

If the water-miscible inorganic oxide network precursor system and the water-miscible liquid composition comprising PFIEP are first contacted together prior to their combination with the organic liquid, some agitation may be required to obtain good contact between these components.

The organic liquid combined with the water-miscible inorganic oxide network precursor system and the water-miscible liquid composition comprising PFIEP in step (a) does not solubilize either the water-miscible inorganic oxide network precursor system (which may be hydrolyzed and/or condensed) or the water-miscible liquid composition of PFIEP. The result of the combination of the organic liquid, the water-miscible mixture inorganic oxide network precursor system and water-miscible liquid composition comprising PFIEP is a two phase liquid system, one phase being the organic liquid and the other phase comprising the water-miscible inorganic oxide network precursor system and the water-miscible liquid composition comprising PFIEP. The amount of organic liquid used can be 10 to 2000%, preferably 25 to 1000% by weight, with reference to the total amount of inorganic oxide network precursor used. Assessment of the amount of organic liquid used also depends in particular on what particle size is being sought for each spherically shaped microcomposite. Generally, less organic liquid is used for coarse particles (spheres with a larger diameter) and more is used for fine particles (spheres with a smaller diameter).

Suitable organic liquids are, e.g. hydrocarbons with 4 to about 40 carbon atoms, such as long chain aliphatic compounds, aromatic compounds or mixtures of aromatic compounds substituted with one or more alkyl groups, e.g. toluene or xylene isomers (separately or in a mixture); chlorinated or fluorinated hydrocarbons; linear or branched alcohols with 6 to 18 carbon atoms; phenols; dialkyl ethers which can be linear or branched, symmetric or asymmetric; di- or tri-ethers (such as dimethyl ether); and ketones which can be symmetric or asymmetric and are predominantly immiscible with water. Preferably, the organic liquid is toluene or o-, m- or p-xylene, separately or as a mixture, or mesitylene, kerosene or cumene.

In step (b) of the present process, the two phase liquid system is agitated sufficiently to sustain a dispersion of the water-miscible phase in the shape of spheres in the organic phase. The temperature at which dispersion of the second water-miscible mixture in the organic liquid is performed and spherical solids are formed from this dispersed phase, generally ranges from about 0° C. to about 100° C.

In step (c) of the present process, the water-miscible inorganic oxide network precursor system is allowed to form a network of inorganic oxide. Network formation is accomplished via gelation of the water-miscible inorganic oxide network precursor system which may in some instances self-initiate due to the presence of the water. In other instances, network formation is allowed by initiating gelation, which can be achieved in a number of ways depending on the PFIEP and the inorganic oxide network precursor selected. Initiation of gelation and the rate of gelation are dependent on a number of factors, such as the amount of water present, pH and the nature of any acid or base used, temperature, pressure, and concentration of the inorganic oxide network precursor. The time required for the network formation can thus vary widely depending on these factors from practically instantaneous to several days.

As discussed above, a larger amount of water can increase the rate of hydrolysis and thus the eventual rate of gelation. However, more water can slow down the rate of gelation when colloidal silica is used because of the dilution factor. A higher concentration of the inorganic oxide network precursor can result in a faster rate of gelation.

Gelation can be carried out over a wide range of acidity and basicity. Network formation can be formed by acid catalyzed gelation (see Sol-Gel Science, Brinker, C. J. and Scherer, G. W., Academic Press, 1990). Although gels can be formed using acid only, the rate of gelation is usually slower when acids are used. Representative examples of suitable catalysts are HCl, $H_3PO_4$, $CH_3COOH$, $NH_3$, $NH_4OH$, NaOH, KOH and $NR^1_3$, wherein $R^1$ represents an alkyl group which contains 1 to 6 carbon atoms. Preferably, a suitable base, such as sodium hydroxide, lithium hydroxide, ammonia, ammonium hydroxide, and organic amines, such as pyridine, are used. The pH adjustment using either acid or base can be achieved in a number of ways and is also dependent on the concentration of acid or base employed. In order to allow network formation to occur, the acid or base can be contacted with either the water-miscible inorganic oxide network precursor system or with the water-miscible liquid composition comprising PFIEP prior to their combination with the organic liquid, or the acid or base can be added to the two-phase liquid system. Some hydrolysis and condensation may occur prior to the formation of the two phase system. However, network formation should be avoided until the three primary components, the water-miscible inorganic oxide network precursor system, the water-miscible liquid composition comprising PFIEP and the organic liquid, of the two phase system are combined and agitated. Thus, preferably, any needed catalyst is added after formation of the two-phase system to allow network formation to occur.

Gelation can be carried out at virtually any temperature at which the water-miscible phase is initially in liquid form. The reaction is typically carried out at room temperature. Raising the temperature can increase the rate of gelation.

Gelling may be initiated at atmospheric pressure or at an excess pressure which corresponds to the sum of the partial pressures of the components of the reaction mixture at the particular temperature being applied. The use of atmospheric pressure is preferred.

After formation, the at least one spherically shaped microcomposite, in the presence or absence of the organic liquid, may optionally be allowed to stand for a period of time. This is referred to as aging. Aging of the wet spherically shaped microcomposite for a few hours to about two (2) days at about room temperature to about 200° C., preferably about 75° C., leads to an increase in pore size and pore volume. This effect is characteristic of silica type gels, where the aging effect gives rise to an increasingly crosslinked network which upon drying is more resistant to shrinkage and thus a higher pore size and higher pore volume results (see, for example, the text Sol-Gel Science, Brinker, C. J. and Scherer, G. W., Academic Press, 1990, pp.518–523).

In step (d), the solid, at least one spherically shaped porous microcomposite formed is recovered from the organic liquid after a sufficient reaction time, at a temperature ranging from room temperature to about 250° C. A sufficient reaction time is the time needed for the sphere to harden sufficiently to maintain its shape when recovered. Recovery of the moist microcomposite sphere from the organic liquid can be accomplished by decanting, filtering or centrifuging.

The spheres can be optionally purified by extraction using azeotropic distillation, i.e. removing the water from the spherically shaped microcomposite and replacing it with an organic solvent, such as an alcohol. This distilled microcomposite may then be further treated hydrothermally. Azeotropic distillation may take place prior to or after recovery of the spherically shaped microcoposite.

After recovery and optional aging, the spherically shaped microcomposites can be optionally dried at a temperature ranging from room temperature to about 250° C., optionally under a protective gas or under vacuum, for a time sufficient to further harden and stabilize the spherically shaped microcomposites. Drying can take place from about 1 hour to about one week.

Preferably, following removal of the organic liquid, the present process further comprises reacidification, washing, filtering or a combination thereof, of the spherically shaped microcomposite. Reacidification, washing, filtering or a combination thereof, may be repeated a number of times. Reacidification of the spherically shaped microcomposite converts, for example, the sodium salt of the perfluorosulfonic acid into the acidic, active form. Suitable acids used for reacidification comprise HCl, $H_2SO_4$ and nitric acid. Washing can be done with deionized water, and the filtering removes excess acid Reacidification, washing, filtering, or a combination thereof can take place at a temperature ranging from room temperature to about 100° C. at atmospheric pressure, and for a time ranging from about one hour to about 24 hours.

A number of reaction variables, for example pH, temperature, aging, method of drying and drying time, have been found to affect the pore size and pore size distribution of the spherically shaped microcomposite. Both higher pH and longer aging of the spherically shaped microcomposite (before solvent removal) lead to larger final pore size in dried spherically shaped microcomposites.

The porous nature of the spherically shaped microcomposite can be readily demonstrated, for example, by solvent absorption. The spherically shaped microcomposite can be observed to emit bubbles which are evolved due to the displacement of the air from within the porous network.

It is believed that the spherically shaped microcomposites of the present invention comprise a continuous network of inorganic oxide having connected porous channels which entraps a highly dispersed PFIEP within and throughout the network. The distribution of the PFIEP entrapped within and throughout the network of inorganic oxide is on a very fine sub-micron scale. The distribution can be investigated using electron microscopy, with energy dispersive X-ray analysis, which provides for the analysis of the elements Si and O (when using silica, for example) and C and F from the PFIEP. The distribution of PFIEP within a spherically shaped microcomposite of the present invention is very uniform.

The spherically shaped microcomposites of the present invention are useful as ion exchange resins, and as catalysts, for example, for alkylating aliphatic or aromatic hydrocarbons, such as the alkylation of naphthalene with propylene; for decomposing organic hydroperoxides, such as cumene hydroperoxide; for sulfonating or nitrating organic compounds; and for oxyalkylating hydroxylic compounds. Other catalytic applications for the spherically shaped microcomposites of the present invention comprise hydrocarbon isomerization and polymerization, such as the isomerization of 1-butene to 2-butenes; carbonylation and carboxylation reactions; hydrolysis and condensation reactions; esterifications and etherifications; hydrations and oxidations; oligomerizations; aromatic acylation; aromatic benzylation; and isomerization and metathesis reactions.

The spherically shaped microcomposite can be used as a catalyst in the isomerization of an olefin. Olefin isomerization is useful in converting compounds into isomers more useful for particular applications. Olefins with the double bond at a terminal end tend to be more reactive and are easy to oxidize which can cause problems with storage. Therefore, a shift to a more stable olefin form can be desirable.

Olefin isomerization processes can be directed towards either skeletal isomerization, double bond isomerization or geometric isomerization. The spherically shaped microcomposite of the present invention can be used as a catalyst for double bond isomerization and some geometric isomerization. Skeletal isomerization is provided to a limited degree at higher temperatures utilizing the spherically shaped microcomposite of the present invention.

The spherically shaped microcomposite can be used as a catalyst with olefins such as $C_4$ to $C_{40}$ hydrocarbons having at least one double bond, the double bond(s) being located at a terminal end, an internal position or at both a terminal and internal position. Most preferred olefins have 4 to 20 carbon atoms. The olefin can be straight-chained (normal) or branched and may be a primary or secondary olefin and thus substituted with one or more groups that do not interfere with the isomerization reaction. Such substituted groups that do not interfere with the isomerization reaction could include alkyl, aryl, halide, alkoxy, esters, ethers, or thioethers. Groups that may interfere with the process would be alcohols, carboxylic acids, amines, aldehydes and ketones.

The spherically shaped microcomposite is contacted with the olefin in a fixed-bed system, a moving-bed system, a fluidized-bed system, or in a batch-type operation. This contacting can be in the liquid phase, a mixed vapor-liquid phase, or a vapor phase, in the absence of hydrogen or in the presence of hydrogen in a molar ratio of hydrogen to olefin of from about 0.01 to about 10. Inert diluents such as helium, nitrogen, argon, methane, ethane and the like can be present either in association with hydrogen or in the absence of hydrogen.

Isomerization conditions using the present spherically shaped microcomposite comprise reaction temperatures generally in the range of about 0° C. to about 300° C., preferably from about 24° C. to about 250° C. Pressure can range from ambient for gas phase or a pressure sufficient to keep reaction in the liquid phase. Reactor operating pressures usually will range from about one atmosphere to about 100 atmospheres, preferably from about one atmosphere to about 50 atmospheres. The amount of catalyst in the reactor will provide an overall weight hourly space velocity (WHSV) of from about 0.1 to 100 hr$^{-1}$, preferably from about 0.1 to 10 hr$^{-1}$; most preferably 0.1 to 2 hr$^{-1}$.

Long contact time during olefin isomerization can create undesirable by-products, such as oligomers. Short contact times ranging from about 0.01 hr to about 10 hrs; preferably 0.1 hr to about 5 hrs can be used with the present spherically shaped microcomposite. Contact time may be reduced at higher temperatures.

Any product recovery scheme known in the art can be used to isolate the resultant olefins. Typically, the reactor effluent will be condensed and the hydrogen and inerts removed therefrom by flash separation. The condensed liquid product then is fractionated to remove light materials from the liquid product. The selected isomers may be separated from the liquid product by adsorption, fractionated, or extraction.

EXAMPLES

NAFION® solutions can be purchased from Aldrich Chemical Co., Milwaukee, Wis., or PFIEP solutions generally can be prepared using the procedure of U.S. Pat. No. 5,094,995 and U.S. Pat. No. 4,433,082. The NAFION® PFIEP solution referred to in the examples below is, unless otherwise noted, NAFION® NR005, a NAFION® solution available from DuPont Fluoroproducts, Fayetteville, N.C., and also known as NAFION® SE-5110, and is prepared from resin which is approximately 6.3 (TFE) molecules for every perfluoro (3,6-dioxa-4-methyl-7-octene sulfonyl fluoride) molecule ($CF_2=CF-O-[CF_2CF(CF_3)]-O-CF_2CF_2-SO_2F$ (PSEPVE)) and has an equivalent weight of approximately 1070. NAFION® NR50 catalyst, the same resin used to prepared the NR005 (SE-5110) solution is available in pellet form from E. I. du Pont de Nemours and Company, Wilmington, Del. (distributed by Aldrich Chemical Company). AMBERLYST 15® sulfonated resin is a registered trademark of Rohm and Haas, Philadelphia, Pa. and is sold commercially by Rohm and Haas.

Example 1

To 40 mls of $Si(OCH_3)_4$ was added 6 g of distilled water and 0.6 g of 0.04M HCl. The mixture was stirred for one hour. 60 ml of a 5 wt % NAFION® solution (the PFIEP) was added to the silicon containing mixture. The mixture was agitated using a twin blade impeller to ensure good mixing. 75 ml of mesitylene was then added and the mixture was stirred. To the rapidly stirred solution 30 ml of 0.4M NaOH was added and the mixture was stirred for a further hour. The product spheres were filtered and dried at 140° C. in vacuum for 2–3 hours. The spheres were washed and reacidified with 3.5M HCl, by covering with about 250 ml of acid and leaving for 1 hour. The spheres were washed with water and the process of reacidification and washing was repeated a total of four times. Finally, the product spheres were placed in about 100 ml of 25 wt % nitric acid and left at 75° C. overnight, followed by filtering and washing with distilled water. The yield was about 18 g. Each spherical particle obtained was in the range of about 0.1 to 1.0 mm in size. The content of PFIEP for each spherical particle was about 13 wt % measured using thermogravimetric analysis (TGA), where the PFIEP was decomposed and removed upon heating to between 400–500° C.

The surface area of a spherical particle was measured to be 316 m$^2$ per g, with a pore volume of 0.5 cc per g, and a pore diameter of 6 nm.

The distribution of the PFIEP within the sphere was very uniform. This was determined by examining a particle which had been placed in epoxy. The particle was polished to show a polished cross section, where the interior of the particle was examined. Energy dispersive X-ray analysis was used to analyze the particle. Elemental analysis showed the presence of Si, O, F and C from the silica network and the PFIEP respectively. The distribution of the PFIEP and silica was examined using a spot mode which analyzed an area of about 100 nm. Larger areas were also examined. The ratio of F and Si was approximately the same in all areas of the particle showing the uniformity.

Example 2

To 40 mls of $Si(OCH_3)_4$ was added 6 g of distilled water and 0.6 g of 0.04M HCl. The mixture was stirred for one hour. 60 ml of a 5 wt % NAFION® solution (the PFIEP) was added to the silicon containing mixture. The mixture was agitated using a twin blade impeller to ensure good mixing. 75 ml of mesitylene was then added and the mixture was stirred. To the rapidly stirred solution 30 ml of 0.4M NaOH was added and the mixture was stirred for a further hour. The mixture, including all of the mesitylene solvent, was placed in ajar. The jar was sealed and placed in an oven at 75° C. to age overnight. The product spheres were then filtered and dried at 140° C. in vacuum for 2–3 hours. The spheres were washed and reacidified with 3.5 M HCl, by covering with about 250 ml of acid and leaving for 1 hour. The spheres were washed with water and the process of reacidification and washing was repeated a total of four times. Finally, the product spheres were placed in about 100 ml of 25 wt % nitric acid and left at 75° C. overnight, followed by filtering and washing with distilled water. The yield was about 18 g. The content of PFIEP of each spherical particle was about 13 wt % measured using TGA. Each spherical particle obtained was in the range of about 0.1 to 1.0 mm in size. The content of PFIEP in each spherical particle was about 13 wt % measured using TGA. The surface area was measured to be 317 m$^2$ per g, with a pore volume of 0.68 cc per g, and a pore diameter of 8.4 nm.

Example 3

To 20 mls of $Si(OCH_3)_4$ was added 3 g of distilled water and 0.3 g of 0.04M HCl. The mixture was stirred for one hour. The mixture was agitated using a twin blade impeller to ensure good mixing. 70 ml of mesitylene was then added and the mixture was stirred. To 30 ml of a 5 wt % "NAFION®" solution (the PFIEP), 15 ml of 0.4 M NaOH was added over about 30 seconds. This PFIEP containing mixture was added to the silicon containing mixture. The resulting mixture was stirred for 1 hour. The product spheres were filtered and dried at 140° C. in vacuum for 2–3 hours. The solid spheres were washed with 3.5M HCl by covering with about 200 ml of acid and leaving for 1 hour. The spheres were washed with water and the process of reacidification and washing was repeated a total of four times. Finally, the product spheres were placed in about 100 ml of 25 wt % nitric acid and left at 75° C. overnight, followed by filtering and washing with distilled water. The yield was about 9 g. Each spherical particle obtained was in the range of about 0.1 to 1.0 mm in size. The content of PFIEP in each spherical particle was about 14 wt % measured using TGA.

Example 4

To 20 mls of $Si(OCH_3)_4$ was added 3 g of distilled water and 0.3 g of 0.04M HCl. The mixture was stirred for one hour. 30 ml of a 5 wt % NAFION® solution (the PFIEP) was added to the silicon containing mixture. The mixture was agitated using a twin blade impeller to ensure good mixing. 75 ml of cumene was then added and the mixture was stirred. To the rapidly stirred mixture, 15 ml of 0.4M NaOH was added and the mixture was stirred for a further hour. The product spheres were filtered and dried at 140° C. in vacuum for 2–3 hours. The solid spheres were washed with 3.5 M HCl, by covering with about 200 ml of acid and leaving for 1 hour. The spheres were washed with water and the process of reacidification and washing was repeated a total of four times. Finally, the product spheres were placed in about 100 ml of 25 wt % nitric acid and left at 75° C. overnight, followed by filtering and washing with distilled water. The yield was about 9 g. Each spherical particle obtained was in the range of about 0.1 to 1.0 mm in size. The content of PFIEP of each spherical particle was about 12.5 wt % measured using TGA.

Example 5

To 40 mls of Si(OCH$_3$)$_4$ was added 6 g of distilled water and 0.6 g of 0.04M HCl. The mixture was stirred for one hour. 60 ml of a 5 wt % NAFION® solution (the PFIEP) was added to the silicon containing mixture. The mixture was agitated using a twin blade impeller to ensure good mixing. 150 ml of white kerosene was then added and the mixture was stirred. To the rapidly stirred mixture, 30 ml of 0.4M NaOH was added and the resulting mixture was stirred for a further hour. The product spheres were filtered and dried at 140° C. in vacuum for 2–3 hours. The solid spheres were washed with 3.5M HCl by covering with about 250 ml of acid and leaving for 1 hour. The spheres were washed with water and the process of reacidification and washing was repeated a total of four times. Finally, the spheres were placed in about 100 ml of 25 wt % nitric acid and left at 75° C. overnight, followed by filtering and washing with distilled water. The yield was about 12 g. Each spherical particle obtained was in the range of about 0.1 to 1.0 mm in size. The content of PFIEP in each spherical particle was about 13 wt % measured using TGA.

Example 6

To 208 g of Si(OCH$_2$CH$_3$)$_4$ (TEOS) was added 54 g of distilled water and 1 g of 0.04M HCl and the mixture was stirred for 40 mins. This TEOS solution was used in the following preparations.

(i) 55 mls of the above mixture was added to 60 ml of a 5 wt % NAFION® solution (the PFIEP). The mixture was agitated using a twin blade impeller to ensure good mixing at a setting of about 30. 200 ml of Kerosene was then added and the mixture was stirred. After about 30 seconds, 40 ml of 0.4M NaOH was added to the rapidly stirred mixture, and the mixture was stirred for a further 15 mins. The product spheres were filtered and dried at 100° C. in a nitrogen flow overnight. The solid spheres were washed with 3.5M HCl by covering with about 200 ml of acid and leaving for about 1 hour. The spheres were washed with water and the process of reacidification and washing was repeated a total of four times. Finally, the spheres were placed in about 100 ml of 25 wt % nitric acid and left at 75° C. overnight, followed by filtering and washing with distilled water. Each spherical particle obtained was in the range of about 0.1 to 0.3 mm in size. The yield was about 9 g. The content of PFIEP in each spherical particle was about 13 wt % measured using TGA.

(ii) 55 mls of the TEOS mixture was added to 60 ml of a 5 wt % NAFION® solution (the PFIEP). The mixture was agitated using a twin blade impeller to ensure good mixing at a setting of about 15. 200 ml of kerosene was then added and the mixture was stirred. After about 30 seconds, 40 ml of 0.4M NaOH was added to the rapidly stirred mixture, and the mixture was stirred for a further 15 mins. The product spheres were filtered and dried at 100° C. in a nitrogen flow overnight. The solid spheres were washed with 3.5 M HCl by covering with about 200 ml of acid and leaving for about 1 hour. The spheres were washed with water and the process of reacidification and washing was repeated a total of four times. Finally the spheres were placed in about 100 ml of 25 wt % nitric acid and left at 75° C. overnight, followed by filtering and washing with distilled water. The yield was about 9 g. Each spherical particle had a larger average particle diameter than in (i) above, i.e., in the range of about 0.1 to 1.0 mm in size. The content of PFIEP in each spherical particle was about 13 wt % measured using TGA.

Example 7

Alkylation of Naphthalene with Propylene over Spherical Shaped Microcomposite

The title reaction was carried out with spherical 13 wt % PFIEP/silica microcomposite of the present invention used as a catalyst and compared with NAFION® catalyst (NR-50) and AMBERLYST-15®. In a 250 ml three neck-flask was added 75 g decalin as solvent, 6.4 g naphthalene (0.05M) and 2.0 g of the solid acid catalyst. Once the reaction temperature of 100° C. was reached, the alkylation reaction as started by bubbling propylene through the naphthalene solution. Liquid sample was taken for gas chromatography (GC) analysis. At 100° C., the naphthalene to propylene molar ratio was determined to be 2.2/1.0 determined by GC. The spherical 13 wt % NAFION® PFIEP/silica microcomposite was the most active catalyst. The results are listed in Table 1. Table 1. Naphthalene conversion (mol %) after 1 hr at 100° C. for the alkylation of naphthalene by propylene over 2 g of solid acid catalyst

TABLE 1

Naphthalene conversion (mol %) after 1 hr at 100° C. for the alkylation of naphthalene by propylene over 2 g of solid acid catalyst

| Catalyst | Conv. % |
| --- | --- |
| Spherical Microcomposite | 42.2 |
| AMBERLYST-15 ® | 10.7 |
| NAFION ® | 6.4 |

Example 8

1-Butene Isomerization to 2-Butenes

1-Butene isomerization to cis-2-butene, trans-2-butene and isobutene was carried out at 22, 50 and 75° C. and ambient pressure with a ½" stainless steel reactor and 5.0 g spherical 13 wt % PFIEP/silica microcomposites of the present invention as a catalyst. Prior to the reaction, the spherically shaped microcomposites were dried in a vacuum oven at 150° C. for overnight. The reaction mixture was analyzed by an on-line GC equipped with a 25 m Plot column coated with Al$_2$O$_3$/KCl (Chrompack Inc., Raritan, N.J.). At room temperature (22° C.), a significant amount of 1-butene was converted to 2-butenes at weight hourly space velocity (WHSV) of 2.5 hr$^{-1}$. n-Butene distribution reached near thermodynamic equilibrium level at 75° C., which is 5.3%, 67.5%, and 27.2% for 1-butene, trans-2-butene, and cis-2-butene, respectively. Isobutene and butene oligomers were produced only in trace amounts under these conditions.

Table 2. Product distribution for the 1-butene isomerization over 5.0 g spherical 13 wt % PFIEP/silica microcomposite under ambient pressure with flow rates of He=110 ml/min and 1-butene=90 ml/min, WHSV of 1-butene=2.5 hr$^{-1}$

TABLE 2

Product distribution for the 1-butene isomerization over 5.0 g spherical 13 wt % PFIEP/silica microcomposite under ambient pressure with flow rates of He = 110 ml/min and 1-butene = 90 ml/min, WHSV of 1-butene = 2.5 hr$^{-1}$

| | Temperature (° C.) | | |
|---|---|---|---|
| % Butenes | 22 | 50 | 75 |
| 1-butene | 87.3 | 25.8 | 6.7 |
| trans-2-butene | 5.2 | 44.8 | 65.9 |
| cis-2-butene | 7.5 | 29.4 | 27.4 |
| isobutene | — | — | — |

Example 9

Alkylation of Toluene with n-Heptene

Both toluene and n-heptene were dried for 24 hours over a 3 A molecular sieve before use. In a round bottom flask was added 15.6 g of toluene and 8.4 g of n-heptene, and a fluoropolymer coated magnetic stirrer was added. A reflux condenser was attached to the flask and a slow stream of nitrogen passed over the top of the reflux condenser to minimize moisture. The flask and contents were heated to 100° C. A sample of 1 g of 13 wt % PFIEP/silica spherically shaped microcomposite was dried in vacuum at 150° C. for 15 hours. The dried spherically shaped microcomposite was added to the toluene/n-heptene mixture, stirred and left to react for two hours. After two hours a sample was removed and the conversion of n-heptene was measured using gas chromatography (GC). In the GC analysis dodecane was used as a standard. The conversion of n-heptene was measured to be 99%, leaving only 1% of the n-heptene unreacted.

Example 10

Benzylation of Benzene and p-Xylene with Substituted Benzyl Alcohol

The benzylation reaction was carried out by heating a stirred mixture of p-methylbenzyl alcohol and benzene or p-xylene, and the solid acid catalyst at a temperature of 80° C. for the benzene mixture and at a temperature of 100° C. for the p-xylene mixture. Solid acid catalysts employed for the benzylation reaction include 13 wt % PFIEP/silica composite in spherical form, NAFION® catalyst (NR-50), and AMBERLYST-15®. For one run, the composition of the mixture was catalyst/alcohol/benzene=2.0/7.5/75 g and for another run the composition of the mixture was catalyst/alcohol/p-xylene=0.5/7.5/75 g. The reaction was carried out with nitrogen flow (at 200 cc/min) or without nitrogen. Liquid samples were taken at certain time intervals and analyzed by a GC equipped with Flame Ionization Detectors (FID). Reaction rate and rate constants were determined.

The acid catalyzed reactions produced the desirable benzylation product, substituted diphenylmethane (I), as well as di-p-methylbenzyl ether (II), the dehydration product from the benzyl alcohol.

The di-p-methylbenzyl ether can be used as the benzylation agent as well. Table 3 lists the product yields (%) after 1 hour of reaction time. Data inside the parentheses are obtained without nitrogen flow. Since flowing nitrogen has a pronounced positive effect on the benzylation reaction, standard runs are all carried out with nitrogen flow.

Table 3. Product yields (%) for the solid acid catalyzed benzylation of benzene and p-xylene with p-methylbenzyl alcohol after 1 hour (catalyst/alcohol/benzene 2.0/7.5/75 g or catalyst/alcohol/p-xylene=0.5/7.5/75 g).

TABLE 3

Product yields (%) for the solid acid catalyzed benzylation of benzene and p-xylene with p-methylbenzyl alcohol after 1 hour (catalyst/alcohol/benzene = 2.0/7.5/75 g or catalyst/alcohol/p-xylene = 0.5/7.5/75 g).

| | in Benzene | | in p-Xylene | |
|---|---|---|---|---|
| Catalyst | I | II | I | II |
| Spherical Microcomposite | 81.6 | 18.4 | 100.00 | 0.0 |
| NAFION ® | 71.2(50.2) | 10.3(33.6) | 66.0(29.6) | 16.3(13.1) |
| AMBERLYST-15 ® | 2.2(1.8) | 1.0(1.2) | 0.5(0.9) | 0.7(1.6) |

What is claimed is:

1. A method for the benzylation of an aromatic compound, comprising: contacting the aromatic compound with a substituted benzyl alcohol in the presence of a spherically shaped porous microcomposite catalyst comprising a perfluorinated ion-exchange polymer containing pendant sulfonic and/or carboxylic acid groups entrapped within and highly dispersed throughout a network of inorganic oxide, wherein the weight percentage of the perfluorinated ion-exchange polymer in the microcomposite is from about 0.1 to about 90 percent, and wherein the size of the pose s in the microcomposite is about 0.5 nm to about 75 nm.

2. The method of claim 1 wherein the aromatic compound is benzene or p-xylene and the substituted benzyl alcohol is p-methylbenzvl alcohol.

* * * * *